United States Patent [19]

Doe, Jr.

[11] Patent Number: 4,704,426
[45] Date of Patent: Nov. 3, 1987

[54] RUBBER COMPOSITIONS CONTAINING AMINE DERIVATIVES OF 1,3,4-THIADIAZOLE

[75] Inventor: Lester A. Doe, Jr., Newtown, Conn.

[73] Assignee: R. T. Vanderbilt Company, Inc., Norwalk, Conn.

[21] Appl. No.: 940,683

[22] Filed: Dec. 11, 1986

[51] Int. Cl.$^4$ .............................................. C08K 5/47
[52] U.S. Cl. ..................................................... 524/83
[58] Field of Search ......................................... 524/83

[56] References Cited

U.S. PATENT DOCUMENTS 2,765,289 10/1956 Fields et al. ................. 252/32.7
2,888,504 5/1959 Broeck, Jr. ............................ 524/83
3,268,347 8/1966 Nagasawa et al. .................... 524/83

OTHER PUBLICATIONS

Kobe et al, *The Mannich Reaction for 2,5-Dimercapto-1,3,4-Thiadiazole*, 37 Croatica Chemica Act, 215–221 (1965).

Primary Examiner—John Kight
Assistant Examiner—Kriellion Morgan
Attorney, Agent, or Firm—Rasma B. Balodis

[57] ABSTRACT

A process is disclosed for stabilization of natural rubber against oxidative degradation in the presence of copper by incorporating therein dairylamine derivatives of 3-hydroxymethyl-5-hydroxymethylthio-1,3,4-thiadiazolidine-2-thione and stabilized rubber compositiions thereof.

3 Claims, No Drawings

RUBBER COMPOSITIONS CONTAINING AMINE DERIVATIVES OF 1,3,4-THIADIAZOLE

BACKGROUND OF THE INVENTION

This invention relates to bifunctional additives for rubber compositions and their use in the stabilization of said compositions. More particularly, the invention relates to rubber compositions that possess a high degree of resistance to the detrimental effects of oxidative aging and metal corrosion over prolonged periods of time.

Essentially all types of rubber are known to be susceptible to deterioration resulting from prolonged exposure to atmospheric oxygen. The major cause of deterioration is the attack of oxygen on the olefinic unsaturation bonds contained in rubber. There is a general agreement that the presence of metals, particularly copper has an overall enchancing effect on the oxidizability of rubber. Although antioxidants have a beneficial effect on the rate of oxidative deterioration, the protective effect is relatively less if metal impurities are present in the rubber composition or the rubber is in contact with metals as, for example, in wire and cable applications.

Depending on the grade and type of rubber, antioxidants are generally selected with regard to the severity of processing and service of the finished article. For added protection, a copper inhibitor is incorporated into the composition.

Among the known antioxidants, arylamines are widely used to protect rubber against oxidative effects. However, arylamine-type antioxidants impart staining and discoloration of the vulcanized rubber. The demand for light colored heavy-duty rubber articles such as white wall tires, fixtures and wires has led to a search for nonstaining, nondiscoloring antioxidants with greater control over metal corrosion.

It has been now discovered that certain diarylamine derivatives of 1, 3, 4-thiadiazole prevent the detrimental effect of both oxygen and copper on the rubber composition. Furthermore, the bifunctional additives are nonstaining and may be used in black as well as light colored rubber articles.

SUMMARY OF THE INVENTION

An aspect of the invention is a rubber composition having incorporated therein a 1,3,4-thiadiazole compound selected from the group consisting of compounds of the structural formula

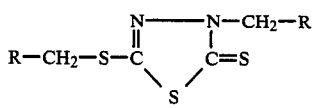

wherein R represents 2,2,4-trimethyl-2,3-dihydroquinolinyl, N-phenothiazinyl, diphenylamino and dialkylphenylamino group having 4 to 9 carbons in the alkyl chain.

Another aspect of the invention is a method of protecting rubber compositions against oxidative deterioration and copper corrosion by incorporating therein the above described 1,3,4-thiadiazole compounds.

DETAILED DESCRIPTION OF THE INVENTION

The additives of the invention may be prepared by reacting a diarylamine with 3-hydroxymethyl-5-hydroxy-methylthio-1,3,4-thiadiazolidine-2-thione according to the following reaction scheme.

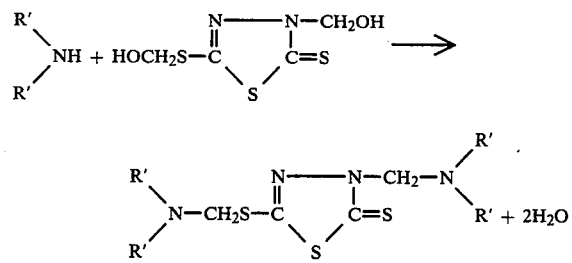

The R' groups represent alkyl and aryl groups which together with the amine nitrogen form R groups defined herein above.

Alternately, the compounds may be prepared by reacting the arylamine with 2,5-dimercapto-1,3,4-thiadiazole and formaldehyde in the presence of an acid and hydrochloric acid.

The additive of the invention may be incorporated into rubber in the amount of about 0.2 to 5 parts per hundred parts rubber (PHR). The effective amount will depend to some extent on the type and grade of rubber used and on the severity of the deteriorating conditions to which the finished article will be exposed.

Rubber that can be protected with the bifunctional additive includes natural rubber such as balata and gutta percha in various forms.

The rubber may be of the black variety containing carbon black fillers and of light variety containing inorganic and mineral fillers such as, among others, titanium dioxide, calcium carbonate, silicate minerals, particularly kaolin clay, whiting, talc and wollastonite. Other compounding ingredients may be added as necessary. The following compounding ingredients, among others, are applicable: accelerators, plasticizers, peptizers, lubricants and processing aids.

The data hereinbelow are intended to illustrate, but not to limit the scope of the invention. Unless otherwise stated, all parts and percentages in the specification and claims are by weight.

EXAMPLE I

A reactor was charged with 30 g (0.20 moles) of 2,5-dimercapto-1,3,4-thiadiazole, 32.4 g (0.40 moles) of formaldehyde (37% aqueous solution) and 250 ml toluene. The mixture was stirred vigorously for 15 minutes. An exothermic reaction occured at 35° C. Then 77.6 g (0.40 moles) of diphenylamine were added and the reaction mixture was heated to reflux. About 28.0 g water was collected by azeotropic distillation in about 1½ to 2 hours, while the reaction temperature reached 112° C. After cooling, toluene was removed with a rotary evaporator giving a brown hard resin having a softening point of 40° C.

EXAMPLE II

A reactor was charged with 42.0 g (0.20 moles) of 3-hydroxymethyl-5-hydroxymethylthio-1,3,4-thiadiazolidine-2thione, 77.6 g (0.40 moles) diphenylamine and 250 ml toluene. The reaction mixture was heated to reflux with stirring. About 28.0 g water was collected by azeotropic distillation in about 1½ to 2 hours. After cooling, toluene was removed with a rotary evaporator. The yield of the product, 3-diphenylaminomethyl-5-diphenylaminomethylthio-1,3,4-thiadiazolidine-2-thione was 102 g.

EXAMPLE III

A 500 ml round bottom flask equipped with a stirrer, thermometer and condenser was charged with 32.0 g (0.20 moles) of 2,5-dimercapto-1,3,4-thiadiazole, 32.5 g (0.40 moles) of formaldehyde (37% aqueous solution) and 150 ml toluene. After stirring for 15 minutes, 68.8 g (0.40 moles) of 2,2,4-trimethyldihydroquinoline were added to the mixture and heated to reflux. About 28.0 g water was collected by azeotropic distillation. The reaction mixture was stripped of volatiles with a rotary evaporator. The yield was 69.0 g of brittle, dark brown resin, 3-(2,2,4-trimethyldihydroquinolinylmethyl)-5-(2,2,4-trimethyldihydroquinolinylmethylthio)-1,3,4-thiadiazolidine-2-thione.

EXAMPLE IV

Test specimens were prepared by compounding natural rubber with additives of the invention and other conventional compounding ingredients. The samples were press cured for 15 minutes at 153° C. After 4 day aging in oxygen bomb at 100° C., the elongation and tensile strength were determined according to ASTM D-412 method. The physical data compiled in Table I show that the specimens containing the compounds of the invention retained the desired properties under oxidative conditions.

EXAMPLE V

Test specimens were prepared by compounding natural rubber with additives of the invention and other conventional compounding ingredients. Copper oleate was added as a controlled impurity. The specimens were cured and after aging at 80° C. for four days, tested according to the methods described in Example III. The data compiled in Table II show that the specimens retained the desired physical properties even in the presence of copper under oxidative conditions.

The above embodiments and illustrations have shown various aspects of the present invention. Other variations will be evident to those skilled in the art and such modifications are intended to be within the scope of the invention as defined in the appended claims.

TABLE I

| Ingredients | Vulcanizates, parts by weight | | | |
|---|---|---|---|---|
| | 1 | 2 | 3 | 4 |
| Smoked sheet rubber | 100.0 | 100.0 | 100.0 | 100.0 |
| K-STAY G[1] | 5.0 | 5.0 | 5.0 | 5.0 |
| Stearic acid | 2.0 | 2.0 | 2.0 | 2.0 |
| Zinc oxide | 5.0 | 5.0 | 5.0 | 5.0 |
| Carbon black | 50.0 | 50.0 | 50.0 | 50.0 |
| Sulfur | 2.5 | 2.5 | 2.5 | 2.5 |
| AMAX[2] | 0.5 | 0.5 | 0.5 | 0.5 |
| 3-Diphenylaminomethyl-5-diphenylaminomethylthio-1,3,4-thiadiazolidine-2-thione | — | 2.0 | — | — |
| 3-(p,p'-Dioctyldiphenylaminomethyl)-5-(p,p'-dioctyldiphenylaminomethylthio)-1,3,4-thiadiazoline-2-thione | — | — | 2.0 | — |
| 3-(N—Phenothiazinylmethyl)-5-(N—phenothiazinylmethylthio)-1,3,4-thiadiazolidine-2-thione | — | — | — | 2.0 |
| Physical properties after cure | | | | |
| Tensile, psi | 3420 | 2900 | 3460 | 2390 |
| Elongation, percent | 600 | 560 | 600 | 500 |
| Hardness | 57 | 60 | 58 | 58 |
| Physical properties after aging | | | | |
| Tensile, percent retained | 25 | 56 | 49 | 39 |
| Elongation, percent retained | 45 | 57 | 58 | 54 |
| Hardness, points changed | 0 | +5 | +2 | +1 |

[1]Rubber processing aid distributed by R. T. Vanderbilt Company, Inc.
[2]N—Oxydiethylene-2-benzothiazolesulfenamide accelerator distributed by R. T. Vanderbilt Company, Inc.

TABLE II

| Ingredients | Vulcanizates, parts by weight | | | | | |
|---|---|---|---|---|---|---|
| | 5 | 6 | 7 | 8 | 9 | 10 |
| Smoked sheet rubber | 100.0 | 100.0 | 100.0 | 100.0 | 100.0 | 100.0 |
| Stearic acid | 2.0 | 2.0 | 2.0 | 2.0 | 2.0 | 2.0 |
| Zinc oxide | 5.0 | 5.0 | 5.0 | 5.0 | 5.0 | 5.0 |
| Titanium dioxide | 50.0 | 50.0 | 50.0 | 50.0 | 50.0 | 50.0 |
| Copper oleate | 0.1 | 0.1 | 0.1 | 0.1 | 0.1 | 0.1 |
| Sulfur | 2.75 | 2.75 | 2.75 | 2.75 | 2.75 | 2.75 |
| Benzothiazyl disulfide | 1.0 | 1.0 | 1.0 | 1.0 | 1.0 | 1.0 |
| Tetramethylthiuram disulfide | 0.1 | 0.1 | 0.1 | 0.1 | 0.1 | 0.1 |
| 3-Diphenylaminomethyl-5-diphenylaminomethylthio-1,3,4-thiadiazolidine-2-thione | — | 3.0 | — | — | — | 1.5 |
| 3-(p,p'-Dioctyldiphenylaminomethyl)-5-(p,p'-dioctyldiphenylaminomethylthio)-1,3,4-thiadiazolidine-2-thione | — | — | 3.0 | — | — | — |
| 3-(N—Phenothiazinylmethyl)-5-(N—phenothiazinylmethylthio)-1,3,4-thiadiazolidine-2-thione | — | — | — | 3.0 | — | — |
| 3-(2,2,4-Trimethyl-2,3-dihydroquinolinylmethyl)-5-(2,2,4-trimethyl-2,3-dihydroquinolinylmethylthio-1,3,4-thiadiazolidine-2-thione | — | — | — | — | 1.5 | — |
| Physical properties after cure | | | | | | |
| Tensile, psi | 3760 | 3800 | 4160 | 3000 | 3760 | 4100 |
| Elongation, percent | 650 | 690 | 670 | 640 | 700 | 700 |
| Hardness | 53 | 51 | 52 | 53 | 47 | 48 |
| Physical properties after aging | | | | | | |
| Tensile, percent retained | Melted | 71 | 48 | 28 | 80 | 76 |
| Elongation, percent retained | | 78 | 66 | 44 | 84 | 83 |

TABLE II-continued

| | Vulcanizates, parts by weight | | | | | |
|---|---|---|---|---|---|---|
| | 5 | 6 | 7 | 8 | 9 | 10 |
| Hardness, points changed | | | 0 | +1 | +2 | 0 | −3 |

What is claimed is:

1. A stabilized composition comprising natural rubber and about 0.2 to 5 parts per hundred parts rubber of a 1,3,4-thiadiazole compound selected from the group consisting of
compounds of the structural formula

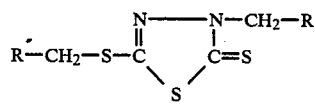

wherein R represents 2,2,4-trimethyl-2,3-dihydroquinolinyl, N-phenothiazinyl, diphenylamino and dialkylphenylamino group having 4 to 9 carbons in the alkyl chain.

2. A composition of claim 1 wherein the 1,3,4-thiadiazole compound is 3-diphenylaminomethyl-5-diphenylaminomethylthio-1,3,4-thiadiazolidine-2-thione.

3. A process for stabilizing rubber against oxidative degradation in the presence of metals which comprises incorporating in the rubber about 0.2 to 5 parts per hundred parts rubber of a 1,3,4-thiadiazole compound selected from the group consisting of
compounds of the structural formula

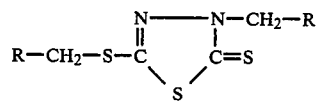

wherein R represent 2,2,4-trimethyl-2,3-dihydroquinolinyl, N-phenothiazinyl, diphenylamino and dialkylphenylamino groups having 4 to 9 carbons in the alkyl chain.

* * * * *

UNITED STATES PATENT AND TRADEMARK OFFICE
CERTIFICATE OF CORRECTION

PATENT NO. : 4,704,426

DATED : Nov. 3, 1987

INVENTOR(S) : Lester A. Doe, Jr.

It is certified that error appears in the above-identified patent and that said Letters Patent are hereby corrected as shown below:

Title page [57]
    "dairylamine derivatives" should be
    --diarylamine derivatives--;

Column 2, lines 66-67
    "3-hydroxymethyl-5-hydroxymethylthio-1,3,4-thiadiazoli-
    dine-2thione" should be
    --3-hydroxymethyl-5-hydroxymethylthio-1,3,4-thiadiazoli-
    dine-2-thione--;

Claim 3, line 21
    "wherein R represent" should be --wherein R represents--.

Signed and Sealed this

Thirty-first Day of May, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO.   :   4,704,426
DATED        :   Nov. 3, 1987
INVENTOR(S)  :   Lester A. Doe, Jr.

It is certified that error appears in the above-identified patent and that said Letters Patent are hereby corrected as shown below:

Title page [21]
  "Appl. No.: 940,683" should be --Appl. No.: 940,688--.

Signed and Sealed this

Fourteenth Day of February, 1989

*Attest:*

DONALD J. QUIGG

*Attesting Officer*    *Commissioner of Patents and Trademarks*